(12) United States Patent
Rozenfeld et al.

(10) Patent No.: US 7,361,134 B2
(45) Date of Patent: Apr. 22, 2008

(54) METHOD AND APPARATUS FOR REAL TIME DOSIMETRY

(75) Inventors: Anatoly Rozenfeld, Redfern (AU); Marc Zaider, New York, NY (US)

(73) Assignee: University of Wollongong, Wollongong (AU)

( * ) Notice: Subject to any disclaimer, the term of this patent is extended or adjusted under 35 U.S.C. 154(b) by 956 days.

(21) Appl. No.: 10/350,357

(22) Filed: Jan. 24, 2003

(65) Prior Publication Data
US 2003/0212302 A1 Nov. 13, 2003

Related U.S. Application Data

(60) Provisional application No. 60/350,951, filed on Jan. 25, 2002.

(51) Int. Cl.
*A61N 5/00* (2006.01)
(52) U.S. Cl. .......................................................... 600/1
(58) Field of Classification Search ................ 600/1–8, 600/427; 128/897, 898, 903, 904
See application file for complete search history.

(56) References Cited

U.S. PATENT DOCUMENTS

| | | | | |
|---|---|---|---|---|
| 5,391,139 | A * | 2/1995 | Edmundson | 600/7 |
| 6,129,670 | A * | 10/2000 | Burdette et al. | 600/427 |
| 6,171,243 | B1 | 1/2001 | Gagnon et al. | |
| 6,311,084 | B1 * | 10/2001 | Cormack et al. | 600/411 |
| 6,429,431 | B1 | 8/2002 | Wilk | |
| 6,431,175 | B1 * | 8/2002 | Penner et al. | 128/899 |

FOREIGN PATENT DOCUMENTS

| | | |
|---|---|---|
| DE | 40 39 619 | 8/1991 |
| DE | 41 38 247 | 5/1993 |
| DE | 41 38 249 | 5/1993 |
| DE | 41 43 401 A1 | 8/1993 |
| WO | WO 99/60921 | 12/1999 |

OTHER PUBLICATIONS

Bradley et al., "Solid state microdosimetry", Nuclear Instruments and Methods in Physics Research B 184 (2001) 135-157.

* cited by examiner

*Primary Examiner*—Samuel G Gilbert
(74) *Attorney, Agent, or Firm*—Stites & Harbison PLLC; Douglas E. Jackson

(57) ABSTRACT

The present invention provides a method of determining the dose rate of a radiation source including locating three or more detectors in the vicinity of said source, each for providing an output indicative of the amount of radiation received from said source and determining the location of said source from at least some of said detector outputs, wherein as many of said detector outputs is required to provide an acceptably accurate result are used in determining said location whereby the dose of radiation from said source can be determined from said determined location of said source and either a known activity of said source or a measure of the activity of said source determined by said detectors.

47 Claims, 4 Drawing Sheets

METHOD AND APPARATUS FOR REAL TIME DOSIMETRY

CROSS REFERENCE TO RELATED APPLICATIONS

This application claims benefit of U.S. Provisional Application No. 60/350,951, filed on Jan. 25, 2002.

FIELD OF THE INVENTION

The present invention relates to a method and apparatus for real time dosimetry, and is of particular but by not exclusive application in the monitoring of the radiation dose during the placement of one or more radiation sources, and for adjusting the placement of subsequent radiation sources on the basis of the results of such dosimetry.

BACKGROUND OF THE INVENTION

With the increasing age and survival of males in the western world and the early diagnosis of prostate cancer, due to the availability of screening (such as PSA screening), prostate cancer has become one of the most commonly diagnosed tumours in the western world. More recently, there has been a large swing away from radical surgical prostatectomy, and a growing preference for treatment by brachytherapy.

Brachytherapy involves the permanent implantation of a plurality of radioactive seeds (each comprising an X-ray source) into the patient's prostate. Ir-192, I-125 and Pd-103 sources are commonly employed. The seeds are implanted one at a time by means of a dedicated type of syringe, and located within the prostate in a predetermined pattern designed to ensure both that the seeds irradiate the appropriate volume of the prostate, and do not irradiate (or minimally irradiate) healthy tissue, most especially outside the prostate. A template is placed against the patient's body with apertures for the syringe, which is inserted through each aperture in turn and, at each of a series of predetermined depths, a seed is released. The procedure is monitored by means of an ultrasound probe located in the rectum, so that the operator can correctly locate the seeds.

However, this existing monitoring technique is highly subjective, and can lead to incorrect dosing of various tissues by as much as a factor of two, and to the excessive dosing of the patient's urethra and rectum. These kinds of complications are very real for treatment of prostate cancer with permanent implants of I-125 or Pd-103 seeds or high dose brachytherapy (HDB) by Ir-192 sources.

The prostate low dose brachytherapy procedure for early stage disease involves the permanent implantation of radioactive seeds into the prostate, normally in the form of I-125 and Pd-103 seeds. Both of these seeds are gamma ray emitters: I-125 ($E_\gamma \sim 27$ keV, $T_{1/2} \sim 60$ days, initial dose rate 8 cGy/h), Pd-103 ($E_\gamma \sim 21$ keV, $T_{1/2} \sim 17$ days, initial dose rate 20 cGy/h). I-125 and Pd-103 implanting, in comparison with other competing treatment modalities such as X-rays from a LINAC, delivers a much higher dose to the target than could safely be administered by an external beam of radiation. Another advantage of using I-125 and Pd-103 seeds is the short tissue penetration of the gamma photons due to the low photon energy of the radiation (half layer is 1.3 cm for I-125 and even less for Pd-103).

Another treatment method, for more advance disease, is high dose rate brachytherapy utilising insertion of a high activity (10 Ci, 400 GBq) Ir-192 source for three to four short fractions.

However, even an ideal pre-implant plan of dose distribution does not guarantee a well delivered dose as may be demonstrated in a post implant evaluation. Misplacement of seeds can often lead to severe complications such as impotence and urinary incontinency, which sometimes arises due to overdosing of the neuro-vascular bundle and urethra.

A clear need exists, therefore, for improved techniques for prostate brachytherapy that allow quality assurance in real time. For interstitial brachytherapy the achievements of local control for prostate cancer is greatly influenced by the dose distribution generated by implanted radionuclide seeds. The treatment plan must be able to deliver the prescribed dose in a tumour, with adequate margins, while minimizing the dose delivered to the surrounding healthy tissues. A sophisticated dose planning procedure for interstitial brachytherapy demands a knowledge of dose distribution around the low dose rate and low X-ray energy radioactive seeds, in the case of I-125 and Pd-103 and high dose rate gamma sources in case of Ir-192. Existing commercial hospital treatment planning systems nevertheless still employ traditional dose calculation formulae in their interstitial brachytherapy source calculation algorithms.

It is an object of the present invention, therefore, to provide an improved dosimetry method and apparatus, which can be used for monitoring radiation dose or source location in a one or more source environment, and which—in one embodiment—can be used to control dose.

SUMMARY OF THE INVENTION

In a first broad aspect, therefore, the present invention provides a method of determining the dose rate or dose of radiation from a radiation source, comprising:

locating three or more detectors in the vicinity of the source, each for providing an output signal indicative of the respective amount of radiation received from said source;

determining the location of the source from at least some of the output signals, wherein as many of the output signals as is required to provide an acceptably accurate result are used in determining the location; and determining the dose rate or dose of radiation from the source from the determined location of the source and either a known activity of the source or a measure of the activity of the source determined with the detectors.

Thus, some detectors may detect relatively small amounts of radiation, and more accurate results may be available by ignoring such detectors and using only the, say, three or four detectors receiving the highest amounts of radiation from the source.

Preferably said method includes locating at least four of said detectors in the vicinity of a radiation source.

With three detectors, in some cases ambiguity may arise in the deduced location of the source. A fourth detector can generally be used to resolve such ambiguity.

Preferably said method includes arranging said detectors so as not all be co-linear.

Preferably said method includes providing said detectors in the form of one or more probes, and more preferably in the form of a plurality of probes, each with the same number of detectors.

The probe or probes may be in the form of a catheter or catheters respectively.

Preferably said method includes employing three of more of said probes, each having three or more of said detectors. More preferably said method includes providing four of said probes, each having four of said detectors.

Preferably said method includes arranging said probes in a substantially regular array in said vicinity.

In one embodiment, said detectors are MOSFET silicon PIN diode, CdZnTe (CZT) or scintillator detectors.

In one embodiment the method includes on-line measurements of dose and dose rate with at least one MOSFET detector.

Preferably said method includes using PIN diode, CZT or scintillator detectors in spectroscopy mode for dosimeter. More preferably the method includes including only photopeaks in the output of each of said PIN or CZT detectors (typically by energy gating the photopeaks).

This will increase the accuracy of the in vivo measurements of direct dose rate from the source, by minimizing the effect of scattered radiation and the energy dependence of attenuation coefficients, and by the use of a tissue equivalent dosimeter.

In one particular embodiment, the method includes determining the dose rate of another radiation source subsequently located in the vicinity of said radiation source, by:
attributing increases in said amounts of radiation detected by said detectors to said other source; and
determining the location of said other source from said increases detected by at least some of said detectors.

Preferably the method includes determining the location of said source from said increases detected by those of said detectors for which the greatest increases are observed. Preferably the method includes using the three or four detectors for which this increase is greatest.

Preferably said determining said location includes taking dose rate to be related to source to detector distance according to the formula:

$$\dot{D}(r) = S_k \Lambda \frac{r_0^2}{r_i^2} g(r) \phi_{an}(r)$$

where $\dot{D}$ is the dose rate, $S_k$ is the air kerma strength in U, $\Lambda$ is the dose rate constant (=0.977 cGy/hr/U for I-125 6711 seeds), $r_0$=1 cm, $r_i$ is a possible distance between said source and the ith detector in cm, $g(r)$ is the radial dose function, and $\phi_{an}(r)$ is the anisotropy factor.

Alternatively, another method for determination of source to detector distance is to use the ratio of areas under any two photopeaks with energy $E_1$ and $E_2$ from radiation source according to formula:

$$R^{E_1/E_2} = Ae^{-br_i}$$

where R is a ratio of areas, i.e counts under the photopeaks with energies of photons $E_1$ and $E_2$, A is an anisotropy coefficient and b is a constant which is equal to difference of mass attenuation coefficients and $r_i$ is a source to detector distance. This will provide another simple method of source to detector distance $r_i$ measurement which then is utilizing in simulation of the seed position.

Preferably said determining said location from values of $r_i$ comprises calculating:

$$\min \sum_{i=1}^{n} \left( \frac{d_i - r_i}{r_i} \right)^2$$

where n is the number of said detectors, and $d_i$ is the actual distances between said source and the ith detector.

Thus, ambiguities in the actual position of the source can be resolved by minimizing the sum of the squares of the percentage difference between the values of $d_i$ and $r_i$. This is a more robust technique than, in the example of four detectors, solving four simultaneous equations exactly.

In a second broad aspect, the present invention provides an apparatus for determining the dose rate or dose of radiation from a radiation source, comprising:
three or more detectors locatable in the vicinity of said source, each for providing an output signal indicative of the respective amount of radiation received from said source; and
a computing mechanism configured to receive said output signals, to determine the location of said source from at least some of said output signals, wherein as many of said output signals as is required to provide an acceptably accurate result are used in determining said locations, and to determine the dose rate or dose of radiation from said source from said determined location of said source and either a known activity of said source or a measure of the activity of said source determined with said output signals.

The computing mechanism may comprise a data collection and processing suite, including—for example—a multichannel analyzer, a computer and associated software.

Preferably said apparatus includes at least four of said detectors.

Preferably said detectors are not all co-linear.

Preferably said apparatus includes one or more probes, each having one or more of said detectors, and more preferably a plurality of probes, each having the same number of detectors.

Preferably said apparatus includes three of more of said probes, each having three or more of said detectors. More preferably said apparatus includes four of said probes, each having four of said detectors.

Preferably the computing mechanism employs substantially only photopeaks from the output signals.

In one particular embodiment, the computing mechanism is operable to:
attribute increases in said detector outputs following the introduction of another radiation source into the vicinity of said radiation source to said other source; and
determine the location of said other source from said increases detected by at least some of said detectors;
whereby said apparatus is operable to determine the dose rate of said other radiation source subsequently located in the vicinity of said radiation source.

Preferably the computing mechanism is operable to determine the location of said other source from said increases detected by those of said detector outputs in which the greatest increases are observed. Preferably the computing mechanism is operable to use the three or four detector outputs for which this increase is greatest.

Preferably the computing mechanism is operable, in determining said location, to take dose to be related to source to detector distance according to the formula:

$$\dot{D}(r) = S_k \Lambda \frac{r_0^2}{r_i^2} g(r) \phi_{an}(r)$$

where $\dot{D}$ is the dose rate, $S_k$ is the air kerma strength in U, $\Lambda$ is the dose rate constant (=0.977 cGy/hr/U for I-125 6711 seeds), $r_0$=1 cm, $r_i$ is a possible distance between said source and the ith detector in cm, g(r) is the radial dose function, and $\phi_{an}(r)$ is the anisotropy factor.

Alternatively, another method for determination of source to detector distance is to use the ratio of areas under any two photopeaks with energy $E_1$ and $E_2$ from radiation source according to the formula:

$$R^{E1/E2} = Ae^{-br_i}$$

where R is a ratio of areas, i.e counts under the photopeaks with energies of photons $E_1$ and $E_2$, A is an anisotropy coefficient and b is a constant which is equal to difference of mass attenuation coefficients and $r_i$ is a source to detector distance. This will provide another simple method of source to detector distance $r_i$ measurement which then is utilizing in simulation of the seed position.

Preferably the computing mechanism is operable to determine said location from values of $r_i$ by first calculating:

$$\min \sum_{i=1}^{n} \left( \frac{d_i - r_i}{r_i} \right)^2$$

where n is the number of said detectors, and $d_i$ is the actual distances between said source and the ith detector.

In a third broad aspect, the present invention provides a method of controlling the positioning of a plurality of radioactive seeds, comprising:

locating three or more detectors in the vicinity of one of said seeds, each of said detectors for providing an output signal indicative of the amount of radiation received from said seeds;

determining the position of said one of said seeds from at least some of said output signals, wherein as many of said output signals as is required to provide an acceptably accurate result are used in determining said position;

adjusting the intended positions of the remainder of said seeds according to the determined position and expected dose rate or dose of said one of said seeds, if necessary; and repeating the above steps for each successive of said seeds.

In a fourth broad aspect, therefore, the present invention provides a method of controlling the total dose of radiation provided by a radiation source, comprising:

locating said source at each of a series of source positions for respective time periods;

locating at least one detector in the vicinity of said source, for providing an output signal indicative of the amount of radiation received from said source at each of said source positions; and progressively determining radiation dose rates or doses due to said source from said output signal corresponding to each of said respective source positions; and controlling each of said successive source positions and time periods according to said radiation dose rates or doses so determined.

Preferably said method includes comparing said progressively determining radiation doses with a schedule of planned doses and varying subsequent positions and periods so that the total dose conforms to a desired total dose, to a desired dose distribution, or to a desired total dose and dose distribution.

Thus, a planned positioning of the seeds can be adjusted as the implantation procedure proceeds, to compensate for inaccuracy in the implantation of successive seeds in, typically, low dose rate brachytherapy where seeds are left in situ. Further, planned source stepping and timing (i.e. dosage) in each source position can be adjusted in each consecutive irradiation, as in the case of high dose rate brachytherapy where generally a single seed is advanced into a patient but subsequently removed.

BRIEF DESCRIPTION OF THE DRAWING

In order that the invention may be more fully ascertained, an embodiment will now be described, by way of example, by reference to the accompanying drawing, in which.

DETAILED DESCRIPTION OF EMBODIMENTS OF THE INVENTION

Figure 1:
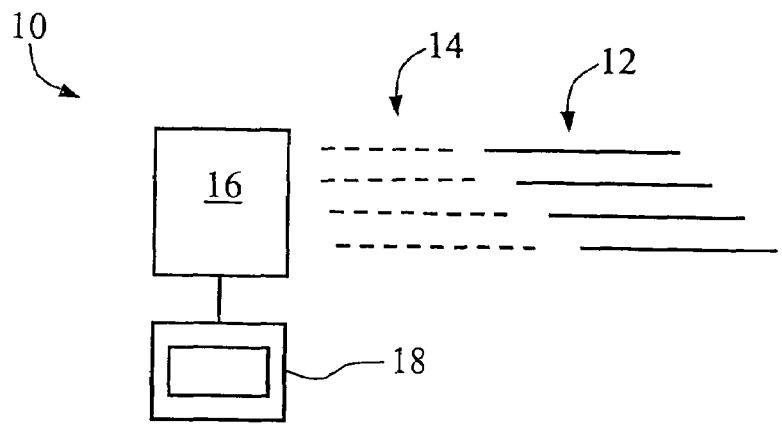
FIG. 1 is a schematic view of a system for determining the dose rate of a radiation source according to one embodiment of the present invention.

In an embodiment of the present invention, there is provided a system for determining the dose rate of a radiation source in vivo during brachytherapy, shown schematically at 10 in FIG. 1.

The system 10 includes four, essentially identical probes in the form of plastic needles 12, connected optically 14 to data collection unit 16. The collection unit 16 is connected to dose-planning and control computer 18, for processing data and producing the final results.

Figure 2A:
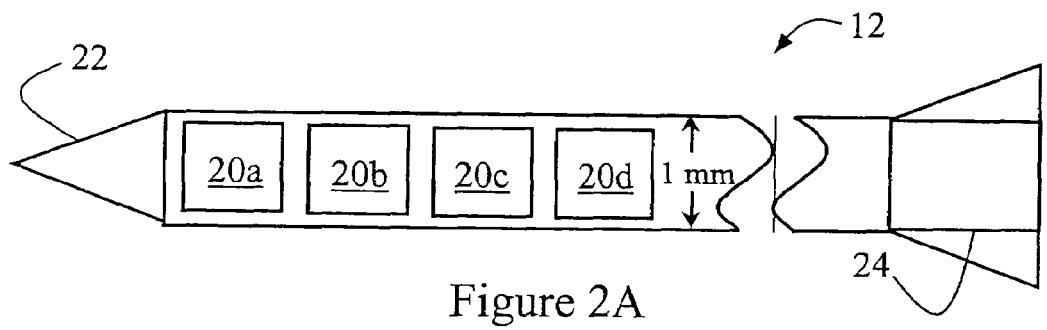
FIG. 2A is a partial cross sectional top view of a detector needle of the system of FIG. 1.

FIG. 2A is a partial top view of a needle 12, in cross section. Each needle 12 has an internal diameter of 1.5 mm, and contains four silicon PIN diode, CdZnTe or scintillator detectors 20a, 20b, 20c and 20d near the head 22 of the needle 12. The detectors 20a, 20b, 20c and 20d thus occupy only a small forward portion of the total length of the needle 12, which may be between 20 and 30 cm in length.

The tail 24 of the needle 12 contains the detector electronics for the detectors 20a, 20b, 20c and 20d.

Certain features of the design of the detectors 20a, 20b, 20c and 20d is dictated by the constraints of their application. The detectors, being designed for dose rate measurements from I-125 or Pd-103 implanted seeds are small enough to be located in the needles 12, have wide dynamic dose rate range of measurements (0.3-20 cGy/h), are sensitive to low energy photons (20-35 keV) below temperatures of 20-40° C. and are able to operate on-line. The detectors 20a, 20b, 20c and 20d are preferably low noise ion implanted silicon detectors working in spectroscopy mode, but—as mentioned above—may be scintillator detectors.

The sensitive volume of each detector is 0.8×3.5×0.3 mm$^3$. The low energy photons 20-35 keV make an essential contribution to the photo-electric effect in silicon or a scintillator, and the estimated count rate in photopeak for this detector is more than 1000 counts/second for a dose rate of 1 cGy/h.

The detector electronics in the needle tail 24 include a spectroscopy preamplifier (based on hybrid AMPTEK™ or NOVA™ brand electronics), used with an optional first field effect transistor (FET) near the detectors inside the needle 12 to reduce noise. Each detector has a low capacitance (of about 1-2 pF), so that the noise of each detector is less than 4 keV under room temperature conditions. The uncertainty in dose rate measurements for 1 cGy/h is less than 3% and can be reduced by multiple readouts of the detector for each seed location. The uncertainty in discrimination of the dose rate increment 0.3 cGy/h on the level 20 cGy/h is better than 30%.

The use of spectroscopy mode and an energy window corresponding to the photopeak of I-125 avoids errors related to the contribution of scattered photons to the detector response. The spectrum of scattered radiation will be changed for different seed-detector positions in tissue, which can affect the detector response due to this photon energy dependence. The detectors are calibrated for particular isotopes in terms of photopeak response, which is taken into account in the algorithms used in subsequent analysis.

Figure 2B:
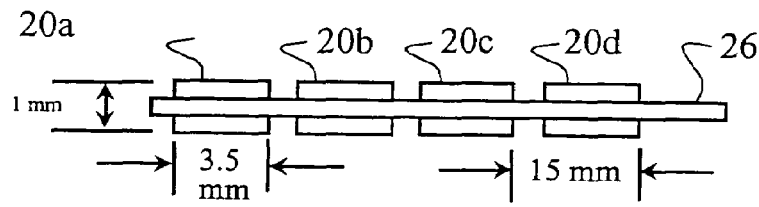
FIG. 2B is a side view of four detector mounted on a Kapton substrate of the detector needle of FIG. 2A.
Figure 2C:
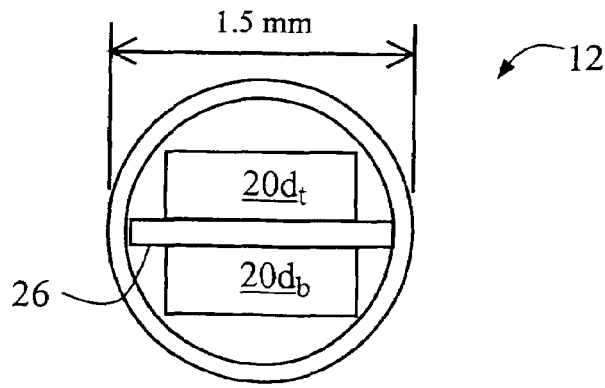
FIG. 2C is a cross sectional end view of the detector needle of FIG. 2A.

FIG. 2B is a side view of the detectors 20a, 20b, 20c and 20d, mounted on a 0.3×1.5×100 mm Kapton substrate 26 (Kapton board being a tissue equivalent substrate ideal for use in these conditions); copper contact pads are used to mount and bond each silicon detector chip and attachment to a hybrid low noise charge sensitive preamplifier (or photodetector where a scintillator-optical fiber detector is employed). FIG. 2C is a cross sectional end view of a needle 12, showing the locating of the Kapton substrate 26 and one of the detectors 20d within the needle 12: $20d_t$ refers to the top segment of detector 20d, $20d_b$ to the bottom segment of detector 20d.

Figure 3:
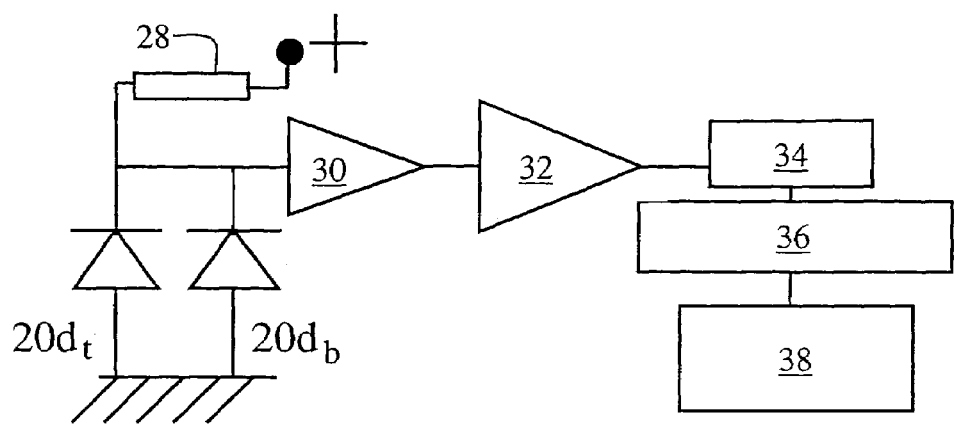
FIG. 3 is a schematic diagram of the electronics set up of one detector channel of the needle of FIG. 2A.

FIG. 3 is a schematic diagram of the electronics set up of one detector channel of a needle 12. In the figure (as in FIG. 2C), $20d_t$ refers to the top segment of detector 20d, $20d_b$ to the bottom segment of detector 20d. The electronics include resistor 28, pre-amplifier 30, amplifier discriminator 32, counter 34, microprocessor 36 and optical RS232 interface 38 (for delivering information on dose rate from each channel to a dose-planning computer 18 for the determination of new seed locations and correction of the next seed position (as will be discussed below). The needles 12 are also controlled by this computer 18.

Alternatively, in those embodiments that employ scintillators, the diodes of FIG. 3 will be replaced with small, high Z scintillators (e.g. CsI(T1) or plastic) attached to a 0.5 mm diameter optical fiber, with a photodiode or photomultiplier at the end of the optic fiber, but with the same readout electronics as—in FIG. 3—are shown after pre-amplifier 30.

Figure 4:
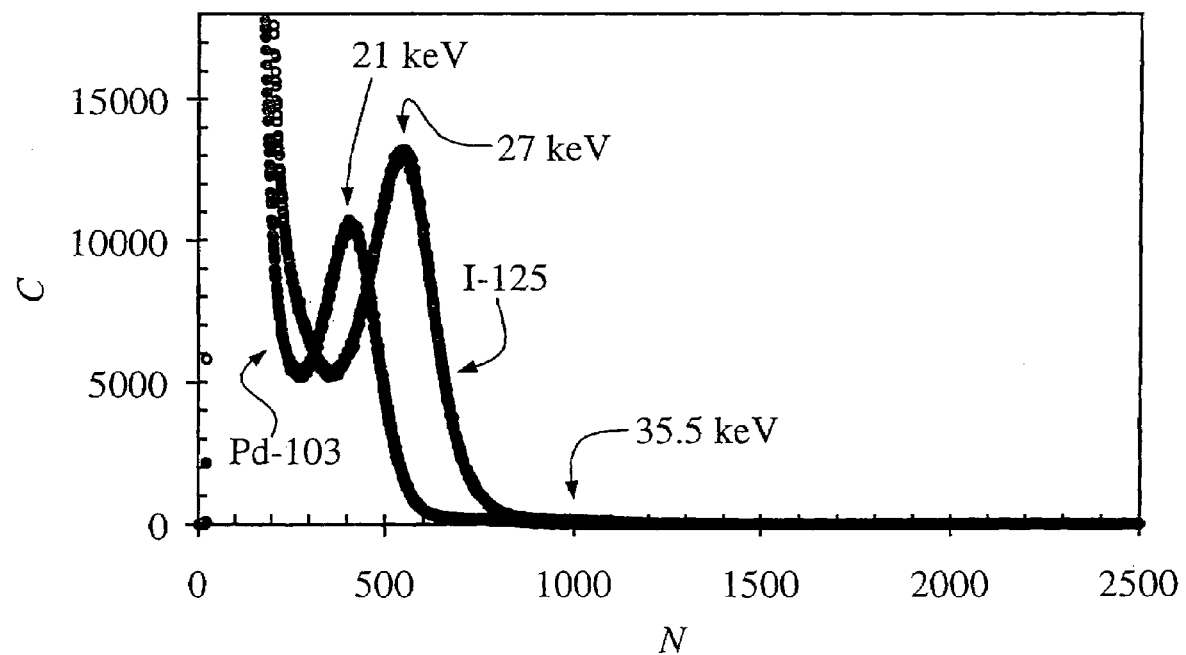
FIG. 4 is a plot of test Pd-103 and I-125 spectra measured with first versions of miniature PIN detectors of the system of FIG. 1.

FIG. 4 is a plot of test spectra measured with the first versions of miniature PIN silicon detectors 20a, 20b, 20c and 20d from Pd-103 (with photopeak at 21 keV) and I-125 (with photopeak at 27 keV), plotted as counts C versus channel number N. The measurement was conducted at room temperature in a perspex prostate phantom. The detector/water dose ratio was constant at any given point in the phantom.

Figure 5:
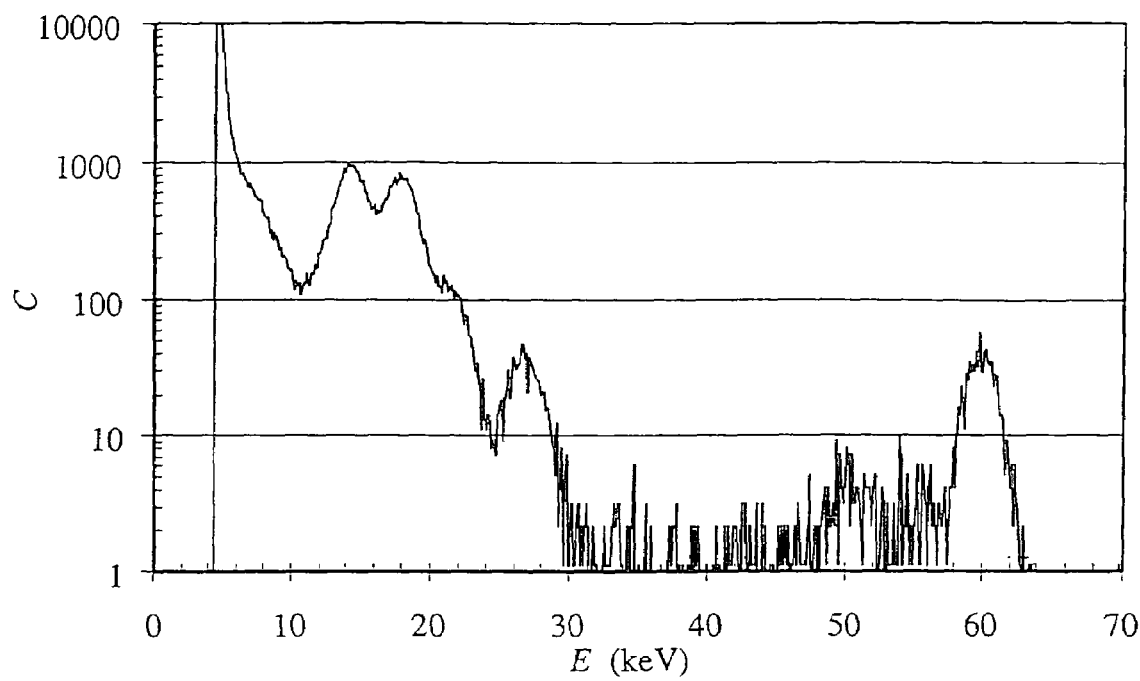
FIG. 5 is a plot of an Am-241 test spectrum measured with $2 \times 2 \times 0.3$ mm$^3$ ion implanted silicon detectors of the system of FIG. 1.

Tests were also conducted with 2×2×0.3 mm ion implanted silicon detectors, under room temperature, and an Am-241 x-ray source with activity 0.1 μCi. The measured spectrum is shown in FIG. 5, plotted logarithmically as counts C versus energy E (keV). Clear photopeaks are visible in the energy range 20-60 keV. The x-ray photopeak at 30 keV on the Compton background from 60 keV photons has an energy resolution of 7%.

Figures 6A, 6B:
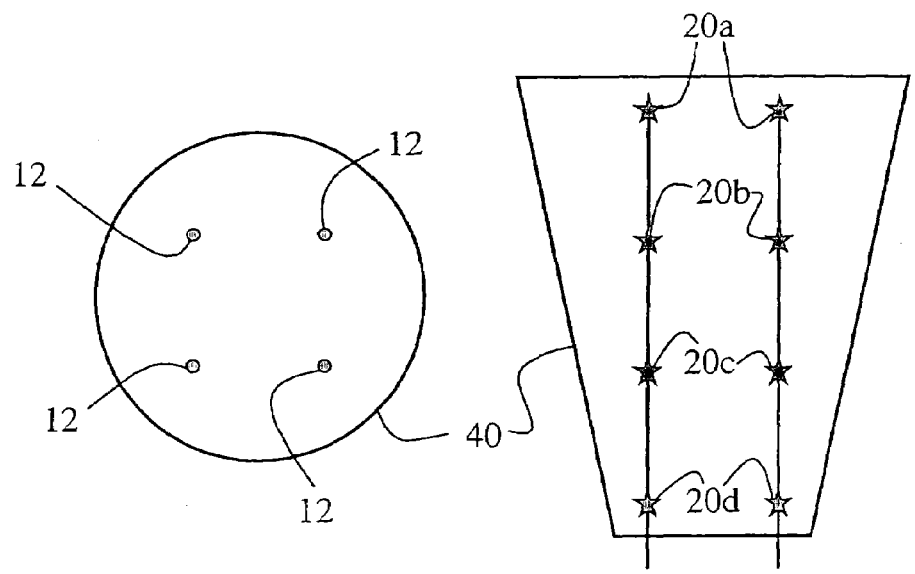
FIGS. 6A and 6B are schematic views (transverse and plan respectively) of four needles of FIG. 2A inserted into a prostrate.

FIGS. 6A and 6B are schematic views (transverse and plan respectively) of the four probe needles 12—each containing four detectors 20a, 20b, 20c and 20d—inserted into a prostrate 40.

The needles 12 would typically be inserted through the same template through which the brachytherapy applicators are inserted for depositing the radioactive seeds. This ensures that the needles 12 are located, themselves, as accurately as possible.

After a seed is deposited to its desired position—or as close as possible thereto—as monitored by means of a ultrasound probe locate in the rectum, readings are taken from each detector in each probe. As will be understood, background counts can also be collected with the needles 12 in situ before the procedure proper, so that background corrections can be performed for each detector. However, as photopeaks are being used for each seed species, such background should in fact be negligible.

The three coordinates of the seed are then deduced from at least three seed to detector distances, derived from the (at least) three detector readings; the seeds are initially assumed to be point sources. When another seed is implanted, the dose readings due to the second seed are the difference between consecutive dose readings. In fact four readings are preferably used, to resolve any ambiguity in the position of the seed, and—for the first seed—the four highest non-collinear and non-coplanar detector outputs are employed, to minimize uncertainty. For subsequent seeds, the four highest differences in outputs of non-collinear/non-coplanar detectors are employed. Actual computation is more complicated, and the algorithm is described in more detail below.

Figure 7:
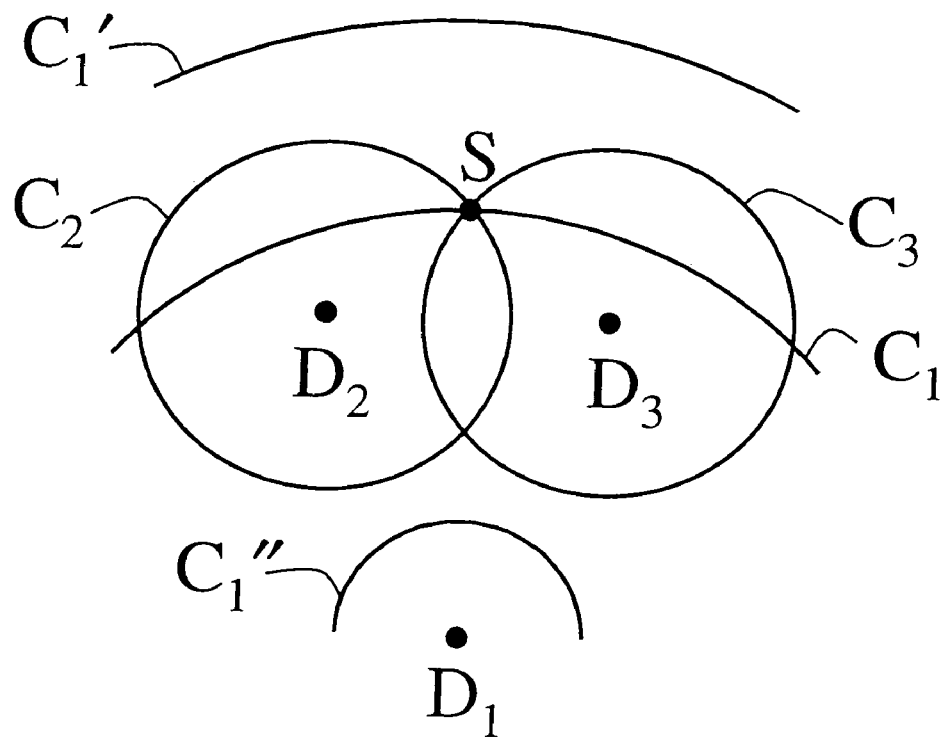
FIG. 7 depicts schematically the relative locations of a seed and three detectors according to the present embodiment of the invention.

The situation is depicted in FIG. 7, in which S is the true seed position and $D_1$, $D_2$ and $D_3$ are three detectors. If all three dose readings were exact, the spheres $C_1$, $C_2$ and $C_3$ (centred in on $D_1$, $D_2$ and $D_3$ respectively with radii corresponding to the dose readings) would intersect at S. If the uncertainty in $D_1$ is too high (i.e. the reading at $D_1$ is low), spheres of much greater or lesser radius $C_1'$ or $C_1''$ respectively would also be consistent with the reading.

This imposes limits on detector separation and sensitivity. The detectors should be located evenly throughout the prostate volume and sufficiently close to one another. For example, referring to FIG. 6, if four needles 12 are inserted, and each needle contains four detectors then, with the detectors 1.5 cm apart, most of the points in the prostate will be within 1.3 cm of the nearest detector. This configuration of detector needles will not interfere with the seed needles inserted closer to the peripheral border of the prostate. With typical iodine source strength of 0.8 U (NIST 1999 standard), the detectors should be able to detect 0.3 cGy/h with reasonable accuracy. This is much lower than typical dose rate in external beam of 300 s\cGy/min that is equal to 18000 cGy/h. If detector sensitivity is lower, the detector spacing can be further reduced to compensate.

On the other hand, each individual detector is required to withstand high dose due to the occasional seed deposited very close to it. It is not unusual to get 20 cGy/h at some detectors. Once a detector reading reaches 20 cGy/h, all subsequent readings of that detector for additional seeds will be even higher, so the detector needs a resolution below 0.3 cGy/h in a reading of 20 cGy/h. Otherwise the detector will be "blinded" by the adjacent seed, and not useful in the reconstruction of subsequent seeds in the same patient.

Another factor to be considered is the dose rate anisotropy of the radioactive seeds. Strictly speaking, it is impossible to deduce the orientation of the prostate seed (line source) from dose rate readings; only the seed to detector distance is obtainable. However, the following procedure (including the equation for dose rate, $\dot{D}$, presented below) is reasonable for establishing seed location, especially when the dose rate anisotropy factor $\phi_{an}(r)$ is known for a particular type of seed, if it is assumed that each seed is deposited with its orientation in the applicator essentially preserved. It should be noted, however, that changes in seed orientation after deposition will introduce some unavoidable uncertainty in seed reconstruction, but this should not be a great source of error.

Figure 8:
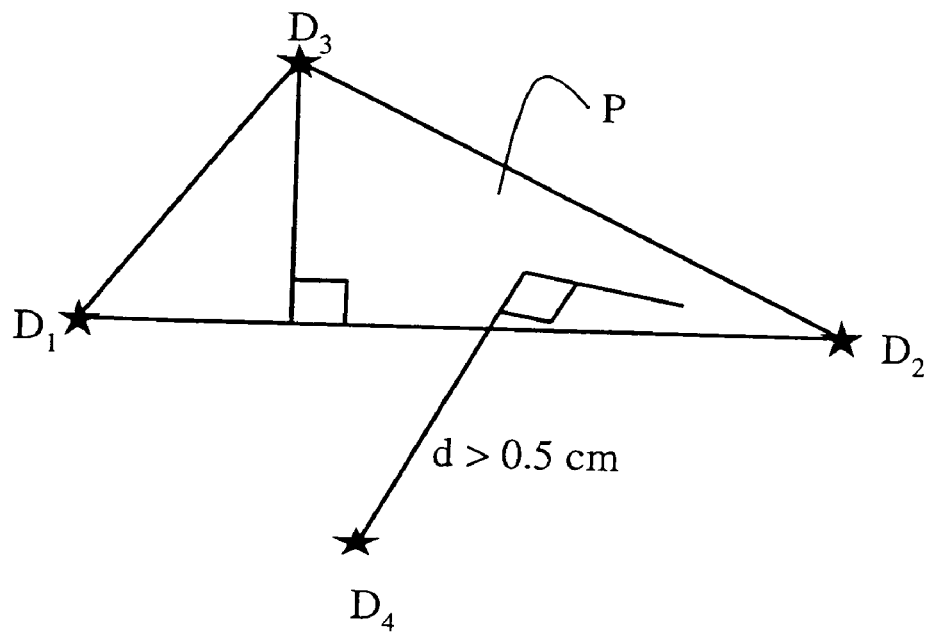
FIG. 8 is a schematic view of four detectors illustrating the criteria for their selection according to the present embodiment of the invention.

Thus, in use the 3D coordinates of detector locations are determined relative to the template, by means of dose rate readings from four detectors to average seed anisotropy effects and reduce anisotropy uncertainty. The first seed implanted into the patient generates dose rate readings in every detector. Referring to FIG. 8, the following are the steps then used to reconstruct the seed position using a first procedure:

1. Sort out the two highest dose rate readings of all detectors. Those two detectors, $D_1$ and $D_2$, will be definitely used.
2. Find the next (i.e. the third) highest reading of which the detector $D_3$ is not collinear with the first two, $D_1$ and $D_2$. Since exact collinearity never happens with uncertainty in detector locations, the criterion of non-collinearity is that the perpendicular distance between $D_3$ and the line joining $D_1$ and $D_2$ is larger than 0.5 cm. Find the next (fourth) highest reading of which the detector $D_4$ is not coplanar with the first three, which means similarly that the perpendicular distance between $D_4$ and the plane defined by the first three detectors is larger than 0.5 cm. The fourth detector outside the 3-detector plane P resolves which of the two possible seed positions is the true one. The distance, $R_{s4}$, between each seed position and the fourth detector is then found. The seed position that gives the same distance as $R_4$ is the true position. Again, the distances will not be exactly the same, so the position that gives the smaller absolute difference between $R_{s4}$ and $R_4$ is the true seed position.
3. From the four dose rate readings, deduce the corresponding seed to detector distances, $R_i$'s, for the four detectors selected by the algorithm.
4. It may then be possible to proceed by solving the simultaneous equations for the seed location:

$$(S_1-D_{1i})^2+(S_2-D_{2i})^2+(S_3-D_{3i})^2=R_i^2 \quad i=1,2,3$$

where $(S_1, S_2, S_3)$ are the 3D seed coordinates to be solved, and $(D_{1i}, D_{2i}, D_{3i})$ are the 3D coordinates of the ith detector. However, it has been found to be more robust, instead, to adopt the following approach. For a point source, the relation between dose rate and seed to detector distance is given by:

$$\dot{D}(r) = S_k \Lambda \frac{r_0^2}{r_i^2} g(r) \phi_{an}(r)$$

where $\dot{D}$ is the dose rate, $S_k$ is the air kerma strength in U, $\Lambda$ is the dose rate constant (=0.977 cGy/hr/U for I-125 6711 seeds), $r_0$=1 cm, $r_i$ is a possible distance between said source and the ith detector in cm, g(r) is the radial dose function, and $\phi_{an}(r)$ is the anisotropy factor.

Alternatively, another method for determination of source to detector distance is to use the ratio of areas under any two photopeaks with energy $E_1$ and $E_2$ from radiation source according to the formula:

$$R^{E1/E2}=Ae^{-br_i}$$

where R is a ratio of areas, i.e counts under the photopeaks with energies of photons $E_1$ and $E_2$, A is an anisotropy coefficient and b is a constant which is equal to difference of mass attenuation coefficients and $r_i$ is a source to detector distance. This will provide another simple method of source to detector distance $r_i$ measurement which then is utilizing in simulation of the seed position.

Next, one determines:

$$\min \sum_{i=1}^{n} \left(\frac{d_i - r_i}{r_i}\right)^2$$

where n is the number of said detectors, and $d_i$ is the actual distances between said source and the ith detector. Thus, ambiguities in the actual position of the source are resolved by minimizing the sum of the squares of the percentage difference between the values of $d_i$ and $r_i$.

Once the position of a seed has been established, the original seed distribution plan is adjusted, if necessary, on the basis of the now known (rather than planned) seed position. If, for example, the seed is found to be a little closer than intended to the urethra, subsequent seeds in that vicinity may be given new, intended locations so that the overall dose to the urethra is within the originally set bounds.

The next seed is then introduced to its revised position, its actual position determined as described above, and—again—original seed distribution plan is adjusted if necessary.

The clinical outcome can be further improved through an on-line, in vivo dose alarming if a serious threat of overdosing the urethra or rectum has appeared during the treatment. This could be provided either by calculating, after each seed is implanted and its position determined, whether the urethra or rectum will indeed receive an excessive dose from the measurements made with the detectors in the needles 12.

Alternatively, a catheter with one or more detectors (or needles) could be placed in the urethra or/and rectum to act solely as an alarm monitor; indeed, in urethra probes a rubber catheter may be preferred, being less painful than a needle.

Modifications within the spirit and scope of the invention may be readily effected by those skilled in the art. It is to be understood, therefore, that this invention is not limited to the particular embodiments described by way of example hereinabove.

The invention claimed is:

1. A method of determining the dose rate or dose of radiation from a radiation source comprising the steps of:
   locating three or more detectors in the vicinity of said source, each for providing an output signal indicative of the respective amount of radiation received from said source;
   determining the location of said source from at least some of said output signals, wherein as many of said output signals as is required to provide an acceptably accurate result are used in determining said location; and
   determining the dose rate or dose of radiation from said source from said determined location of said source and either a known activity of said source or a measure of the activity of said source determined with said detectors.

2. The method according to claim 1, comprising locating at least four of said detectors in the vicinity of a radiation source.

3. The method according to claim 1, comprising arranging said detectors so as not to be all co-linear.

4. The method according to claim 1, comprising providing one or more probes, each having one or more of said detectors.

5. The method according to claim 4, further comprising employing three or more of said probes, each having three or more of said detectors.

6. The method according to claim 4, wherein the one or more probes are in the form of a catheter or catheters.

7. The method according to claim 4, further comprising providing four of said probes each having four of said detectors.

8. The method according to claim 4, comprising arranging said probes in a substantially regular array in said vicinity.

9. The method according to claim 1, comprising providing a plurality of probes, each having an equal number of said detectors.

10. The method according to claim 1, wherein said detectors are MOSFET silicon PIN diode, CdZnTe (CZT) or scintillator detectors.

11. The method according to claim 1, including on-line measurements of dose and dose rate with at least one MOSFET detector.

12. The method according to claim 1 using PIN diode, CZT or scintillator detectors in spectroscopy mode for dosimetry.

13. The method according to claim 12, comprising using only photopeaks in the output signal of each of said detectors.

14. The method according to claim 1, further comprising determining the dose rate of another radiation source subsequently located in the vicinity of said radiation source by:
   attributing increases in said amounts of radiation detected by said detectors to said other source; and
   determining the location of said other source from said increases detected by at least some of said detectors.

15. The method according to claim 14, comprising determining the location of said other source from said increases detected by those of said detectors for which the greatest increases are observed.

16. The method according to claim 15, comprising using three or four detectors for which this increase is greatest.

17. The method according to claim 14, wherein said determining of said location of said other source includes taking dose rate to be related to source-to-detector distance according to the formula $$\dot{D}(r) = S_k \Lambda \frac{r_0^2}{r_i^2} g(r) \phi_{an}(r)$$

where $\dot{D}$ is the dose rate, $S_k$ is the air kerma strength in U, $\Lambda$ is the dose rate constant, $r_0=1$ cm, $r_i$ is a possible distance between said other source and the ith detector in cm, $g(r)$ is the radial dose function, and $\phi_{an}(r)$ is the anisotropy factor.

18. The method according to claim 14, comprising calculating the source-to-detector distance by using the ratio of areas under any two photopeaks with energy $E_1$ and $E_2$ from said other source according to the formula:

$$R^{E_1/E_2} = Ae^{-br_i}$$

where R is a ratio of areas under the photopeaks with energies of photons $E_1$ and $E_2$, A is an anisotropy coefficient and b is a constant which is equal to difference of mass attenuation coefficients and $r_i$ is a source to detector distance.

19. The method according to claim 17, wherein said determining of said location from values $r_i$ comprises calculating:

$$\min \sum_{i=1}^{n} \left( \frac{d_i - r_i}{r_i} \right)^2$$

where n is the number of said detectors, and $d_i$ is the actual distances between said source and the ith detector.

20. An apparatus for determining the dose rate or dose of radiation from a radiation source comprising:
   three or more detectors locatable in the vicinity of said source, each for providing an output signal indicative of the respective amount of radiation received from said source;
   a computing mechanism configured to receive said output signals, to determine the location of said source from at least some of said output signals, wherein as many of said output signals as is required to provide an acceptably accurate result are used in determining said location, and to determine the dose rate or dose of radiation from said source from said determined location of said source and either a known activity of said source or a measure of the activity of said source determined with said output signals; and
   a plurality of probes, each having an equal number of detectors.

21. The apparatus according to claim 20, wherein said computing mechanism comprises a data collection processing suite.

22. The apparatus according to claim 20, wherein the apparatus includes at least four of said detectors.

23. The apparatus according to claim 20, wherein said detectors are not all co-linear.

24. The apparatus according to claim 20, wherein the apparatus includes four of said probes each having four of said detectors.

25. The apparatus according to claim 20, wherein said detectors are MOSFET silicon PIN diode, CdZnTe or scintillator detectors.

26. The apparatus according to claim 20, wherein said computing mechanism employs substantially only photopeaks from said output signals.

27. The apparatus according to claim 20, wherein said computing mechanism is operable to:
attribute increases in said output signals following the introduction of another radiation source into the vicinity of said radiation source to said other source; and
determine the location of said other source from said increases detected by at least some of said detectors;
whereby said apparatus is operable to determine the dose rate of said other radiation source, subsequently located in the vicinity of said rotation source.

$$\min \sum_{i=1}^{n} \left( \frac{d_i - r_i}{r_i} \right)^2.$$

28. An apparatus as claimed in claim 20, wherein said detectors operate in spectroscopy mode.

29. A method of controlling the positioning of a plurality of radioactive seeds, comprising:
locating three or more detectors in the vicinity of one of said seeds, each of said detectors providing an output signal indicative of the amount of radiation received from said seed;
determining the position of said one of said seeds from at least some of said output signals, wherein as many of said output signals as is required to provide an acceptably accurate result are used in determining said position;
adjusting the intended position of the remainder of said seeds according to the determined position and expected dose rate or dose of said one of said seeds, if necessary; and
repeating the above steps for each successive of said seeds.

30. A method of controlling the total dose of radiation provided by a radiation source, comprising:
locating said source at each of a series of source positions for respective time periods;
locating at least one detector in the vicinity of said source, for providing an output signal indicative of the respective amount of radiation received by said detector from said source at each of said source positions;
progressively determining a radiation dose rate or dose due to said source from said output signal corresponding to each of said respective source positions; and
controlling each of said successive positions and periods according to said radiation dose rates or doses so determined.

31. The method according to claim 30, including comparing said progressively determined radiation dose rates or doses with a schedule of planned dose rates or doses and varying subsequent source positions and time periods so that the total dose conforms to a desired total dose, to a desired dose distribution, or to a desired total dose and dose distribution.

32. An apparatus for determining the dose rate or dose of radiation from an in vivo source of low energy X-rays, comprising:
a catheter for locating in a urethra or rectum and having at least one radiation detector;
a spectrometer for receiving an output of said detector; and
a data processor for receiving an output of said spectrometer;
wherein said apparatus is configured to determine from an area under one or more photopeaks of said low energy X-rays a dose rate or dose delivered by said source.

33. An apparatus as claimed in claim 32, adapted for use with a source comprising one or more I-125 seeds.

34. An apparatus as claimed in claim 33, wherein said area is about a photopeak of 27 keV.

35. An apparatus as claimed in claim 32, adapted for use with a source comprising one or more Pd-103 seeds.

36. An apparatus as claimed in claim 35, wherein said area is about a photopeak of 21 keV.

37. An apparatus as claimed in claim 32, wherein said at least one radiation detector comprises one or more non water equivalent detectors, and said processor is configured to provide water equivalent dosimetry by employing a calibration measurement made in water or in a water equivalent material.

38. An apparatus as claimed in claim 37, wherein said one or more non water equivalent detectors comprise semiconductor silicon, CZT or scintillator spectroscopy detectors.

39. An apparatus for determining the dose rate or dose of radiation from a radiation source comprising:
three or more detectors locatable in the vicinity of said source, each for providing an output signal indicative of the respective amount of radiation received from said source;
a computing mechanism configured to receive said output signals, to determine the location of said source from at least some of said output signals, wherein as many of said output signals as is required to provide an acceptably accurate result are used in determining said location, and to determine the dose rate or dose of radiation from said source from said determined location of said source and either a known activity of said source or a measure of the activity of said source determined with said output signals; and
three or more probes, each having three or more of said detectors.

40. An apparatus for determining the dose rate or dose of radiation from a radiation source comprising:
three or more detectors locatable in the vicinity of said source, each for providing an output signal indicative of the respective amount of radiation received from said source; and
a computing mechanism configured to receive said output signals, to determine the location of said source from at least some of said output signals, wherein as many of said output signals as is required to provide an acceptably accurate result are used in determining said location, and to determine the dose rate or dose of radiation from said source from said determined location of said source and either a known activity of said source or a measure of the activity of said source determined with said output signals; and
wherein said computing mechanism employs substantially only photopeaks from said output signals.

41. An apparatus for determining the dose rate or dose of radiation from a radiation source comprising:

three or more detectors locatable in the vicinity of said source, each for providing an output signal indicative of the respective amount of radiation received from said source; and a computing mechanism configured to receive said output signals, to determine the location of said source from at least some of said output signals, wherein as many of said output signals as is required to provide an acceptably accurate result are used in determining said location, and to determine the dose rate or dose of radiation from said source from said determined location of said source and either a known activity of said source or a measure of the activity of said source determined with said output signals; and wherein said computing mechanism is operable to:
attribute increases in said output signals following the introduction of another radiation source into the vicinity of said radiation source to said other source; and
determine the location of said other source from said increases detected by at least some of said detectors;
whereby said apparatus is operable to determine the dose rate of said other radiation source subsequently located in the vicinity of said rotation source.

42. The apparatus according to claim 41, wherein said computing mechanism is operable to determine the location of said other source from said increases detected by those of said output signals in which the greatest increases are observed.

43. The apparatus according to claim 42, wherein said computing mechanism is operable to use the output signals of three or four of said detectors for which this increase is greatest.

44. The apparatus according to claim 41, wherein said computing mechanism is operable, in determining said location, to take dose to be related to source-to-detector distance according to the formula:

$$\dot{D}(r) = S_k \Lambda \frac{r_0^2}{r_i^2} g(r) \phi_{an}(r)$$

where $\dot{D}$ is the dose rate, $S_k$ is the air kerma strength in U, $\Lambda$ is the dose rate constant, $r_0 = 1$ cm, $r_i$ is a possible distance between said source and the ith detector in cm, $g(r)$ is the radial dose function, and $\phi_{an}(r)$ is the anisotropy factor.

45. The apparatus according to claim 44, wherein said computing mechanism is operable to determine said location from values of $r_i$ by first calculating them from the formula:

$$\min \sum_{i=1}^{n} \left( \frac{d_i - r_i}{r_i} \right)^2$$

46. The apparatus according to claim 41, wherein the source-to-detector distance is calculated by using the ratio of areas under any two photopeaks with energy $E_1$ and $E_2$ from radiation source according to the formula:

$$R^{E_1/E_2} = A e^{-b r_i}$$

where R is a ratio of areas under the photopeaks with energies of photons $E_1$ and $E_2$, A is an anisotropy coefficient and b is a constant which is equal to difference of mass attenuation coefficients and $r_i$ is a source to detector distance.

47. An apparatus for determining the dose rate or dose of radiation from a radiation source comprising:
three or more detectors locatable in the vicinity of said source, each for providing an output signal indicative of the respective amount of radiation received from said source; and
a computing mechanism configured to receive said output signals, to determine the location of said source from at least some of said output signals, wherein as many of said output signals as is required to provide an acceptably accurate result are used in determining said location, and to determine the dose rate or dose of radiation from said source from said determined location of said source and either a known activity of said source or a measure of the activity of said source determined with said output signals; and
wherein said detectors operate in spectroscopy mode.

* * * * *